(12) United States Patent
Singh

(10) Patent No.: US 8,298,213 B2
(45) Date of Patent: Oct. 30, 2012

(54) MEDICAL INSTRUMENT

(76) Inventor: Steven Jiwan Singh, WoodVale WA (AU)

( * ) Notice: Subject to any disclaimer, the term of this patent is extended or adjusted under 35 U.S.C. 154(b) by 1694 days.

(21) Appl. No.: 11/614,173

(22) Filed: Dec. 21, 2006

(65) Prior Publication Data

US 2008/0154244 A1 Jun. 26, 2008

(51) Int. Cl.
*A61B 1/303* (2006.01)
(52) U.S. Cl. ............ 606/1; 600/204; 600/562; 600/564; 600/570; 604/264; 604/275; 604/278; 604/279; 604/164.01; 604/174; 606/119
(58) Field of Classification Search ................. 606/1
See application file for complete search history.

(56) References Cited

U.S. PATENT DOCUMENTS

| | | | |
|---|---|---|---|
| 3,176,728 A * | 4/1965 | Baumann | ................. 141/199 |
| 4,000,743 A | 1/1977 | Weaver | |
| 5,209,754 A | 5/1993 | Ahluwalia | |
| 5,368,598 A | 11/1994 | Hasson | |
| 5,603,689 A | 2/1997 | Lucini | |
| 5,797,899 A | 8/1998 | Tilton, Jr. | |
| 5,840,077 A | 11/1998 | Rowden et al. | |
| 6,174,317 B1 | 1/2001 | Engman | |
| 6,235,037 B1 | 5/2001 | East et al. | |
| 6,264,604 B1 | 7/2001 | Kieturakis et al. | |
| 6,423,075 B1 * | 7/2002 | Singh et al. | ................. 606/119 |
| 2002/0099263 A1 | 7/2002 | Hale et al. | |

* cited by examiner

*Primary Examiner* — Aaron Roane
(74) *Attorney, Agent, or Firm* — Allen, Dyer, Doppelt, Milbrath & Gilchrist, P.A.

(57) ABSTRACT

A medical instrument comprises a funnel having a tube with opposite first and second ends, respectively, with a conical portion at the first end. Conical portion has an outer conical surface which increases in outer diameter in a direction from the second end to the first end. A mouth is provided at an end of the conical portion distant to the end, and a lip extends about a part of the circumference of the mouth. The lip protrudes from the conical surface. A first grip is formed axially along the tube and provides a visual reference to the lip.

13 Claims, 4 Drawing Sheets

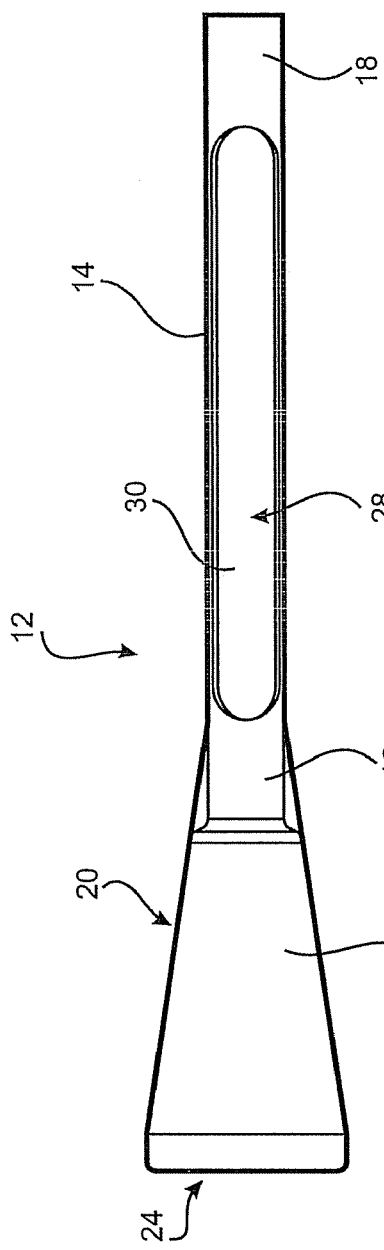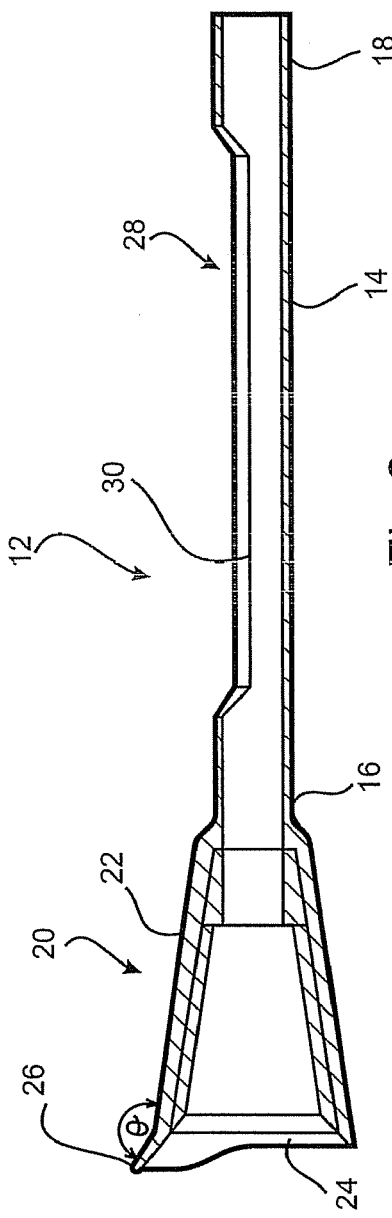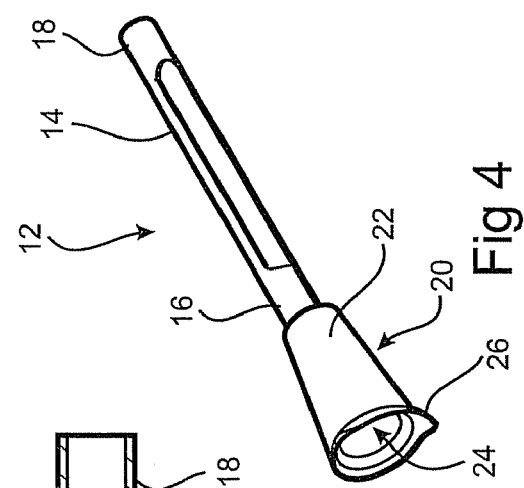

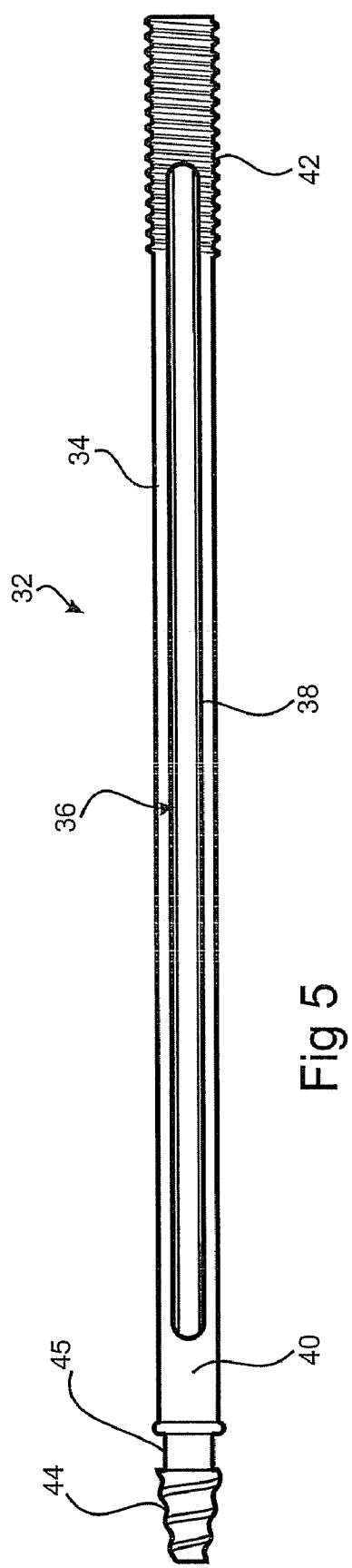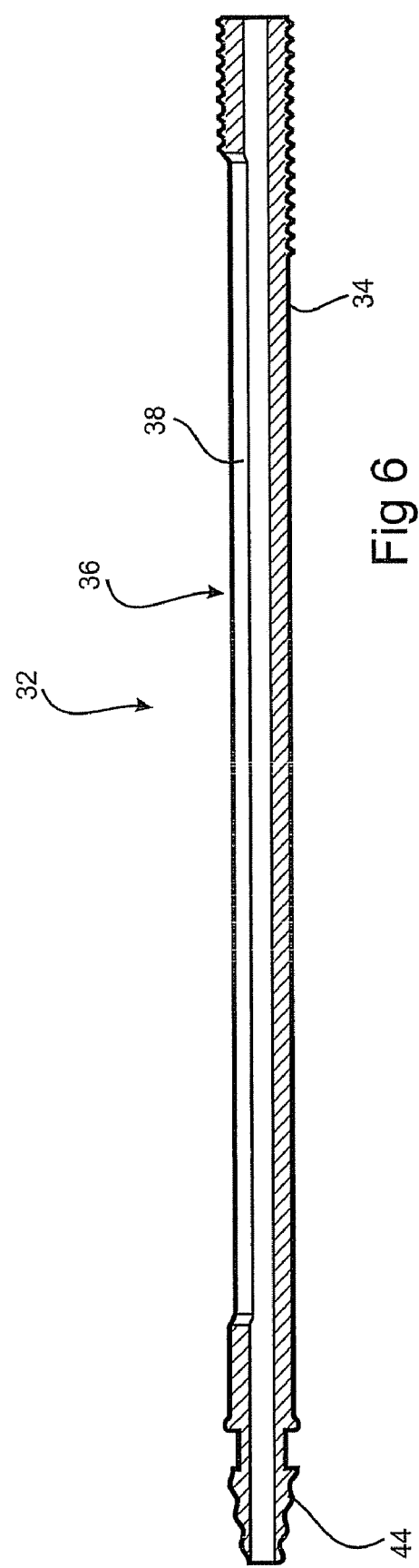

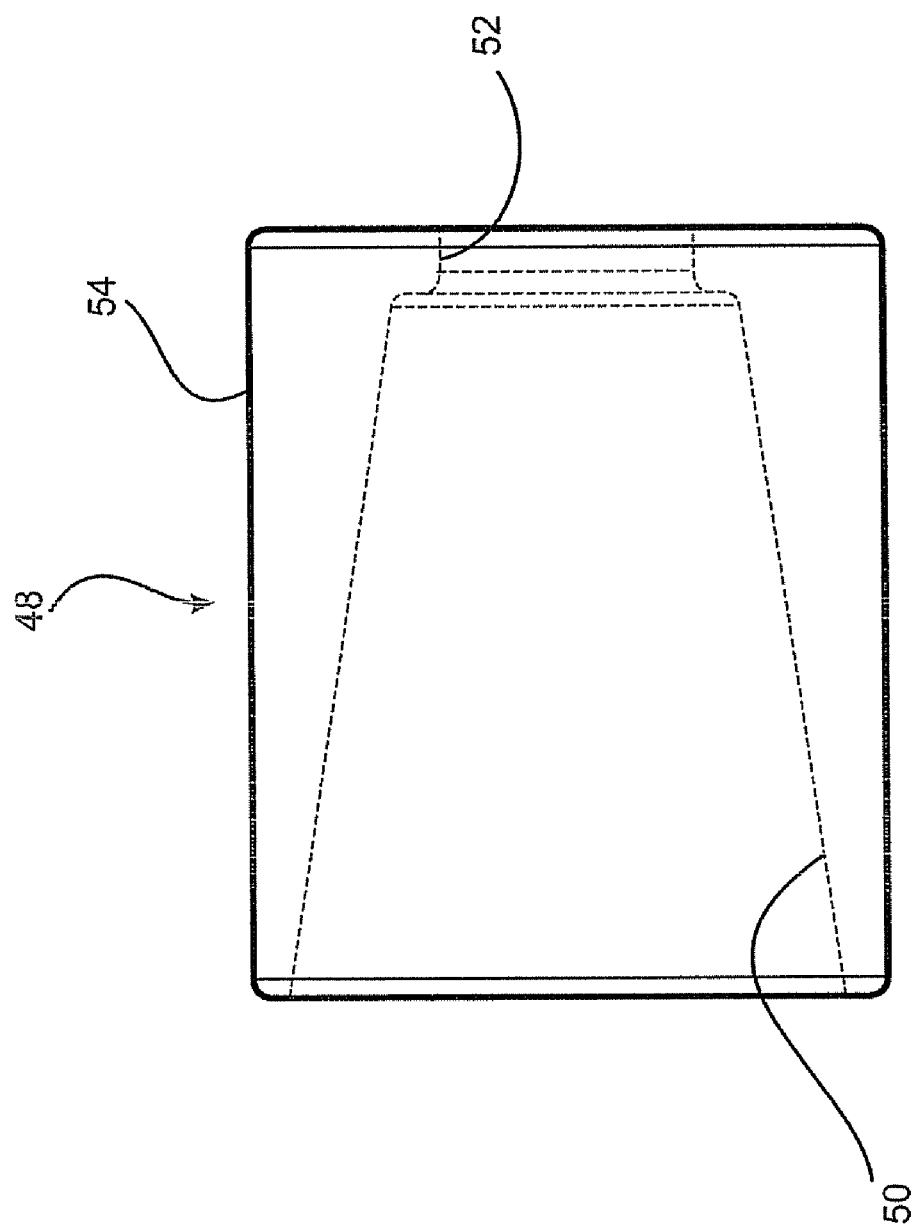

MEDICAL INSTRUMENT

FIELD OF THE INVENTION

The present invention relates to a medical instrument which may be used in, general surgery, gynaecological surgery or non-surgical procedures.

BACKGROUND OF THE INVENTION

Australian Patent No. 773391, and equivalent U.S. Pat. No. 6,423,075 owned by the present applicant, describes a surgical instrument for gynaecological laparoscopy. The instrument comprises a cervical funnel and an intra-uterine cannula. The funnel has an elongate hollow tube with a cone-shaped member at one end. The outer diameter of the cone-shaped member increases in the direction of insertion of the funnel into the vagina. A lip is formed about a portion of a circumference of a mouth of the cone-shaped member and protrudes from an outer surface of the cone-shaped member. The cone-shaped member is typically made from a plastics material to allow electrocautery of the vaginal vault with an electric current, while the hollow tube is made from surgical grade stainless steel to allow autoclaving.

The intra-uterine cannula is in the form of an outer hollow sheath having a conical thread at one end. The conical thread is designed to screw into the cervix and thus form a seal with the uterus. The inter-uterine cannula is slidably and rotatably held within the cervical funnel with the conical thread extending beyond the cone-shape member. A manipulation shaft is in turn slidably and rotatably held within the outer sheath.

The above-described instrument has been successfully used for many years in gynaecological surgery. The present invention has evolved from a desire to improve the aforementioned instrument. However, while the above prior art instrument is described in relation to gynaecological surgery it is not intended that embodiments of the present invention be limited to such use. It is envisaged that embodiments of the present invention may also be used in general surgery or non surgical procedures.

It is to be understood that, if any prior art publication is referred to herein, such reference does not constitute an admission that the publication forms a part of the common general knowledge in the art, in Australia or any other country.

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

SUMMARY OF THE INVENTION

According to the present invention, there is a provided a medical instrument that may comprise a funnel having an elongated tubular portion with opposite first and second ends and a conical portion at the first end, the conical portion having a conical outer surface which increases in outer diameter in a direction from the second end to the first end, a mouth at an end of the conical portion distant to the first end of the elongated tubular portion, and a lip that extends about a part of a circumference of the mouth and protrudes from the conical outer surface, and a first grip formed on the elongated tubular portion, the first grip positioned to provide a visual reference to a position of the lip.

The first grip may comprise a portion that extends axially along a length of the tubular portion. In one embodiment, the portion of the first grip extends in alignment with a mid-point of an arc length of the lip. The portion of the first grip may be in the form of one or more mutually aligned grooves. However, in an alternative embodiment the portion of the first grip may comprise one or more cut-outs in the tubular portion. It is believed that manufacture of the instrument may be simplified if the first grip is formed as a single elongated cut-out.

When the instrument is used in surgery or non-surgical examination procedures such as examinations it may further comprise a plug having an inner surface of complementary shape and configuration to the conical outer surface; and, a central bore, whereby the elongated tubular portion passes through the central bore, and the inner surface when pushed onto the outer surface, forms a seal therewith. The plug may also comprise an outer cylindrical surface which forms a seal with surrounding tissue of a body cavity or opening to thereby plug the cavity or opening. When used in gynaecological procedures the tissue comprises a vaginal wall, wherein the plug plugs the vagina.

It is envisaged that the funnel is formed as a single, or one-piece, device. In this embodiment, the funnel may be made from a plastics material. Moreover, the funnel may be made by a moulding process.

The medical instrument may further comprise a cannula having an outer sheath dimensioned to slide axially through, and be rotatable within, the elongated tubular portion, the cannula provided with a second grip extending axially along a length of the outer sheath. The second grip may comprise a portion in the form of one or more axially extending grooves, or one or more axially extending cut-outs, in the outer sheath. When the portion of the second grip comprises more than one groove or more than one cut-out, two or more of the grooves or the cut-outs may be axially aligned. In perhaps a simplest form of the cannula, the second grip may be in the form of a single elongated cut-out having opposite ends that terminate inside of respective opposite ends of the outer sheath; that is, in this form the second grip may be in the form of an elongated slot.

The cannula has: first and second ends, a conical screw near the first end for screwing into an opening of, or formed in, an organ or other tissue, the conical screw reducing in diameter in a direction from the second end to the first end; and, a neck located between the conical screw and the first end of the cannula, the neck having a diameter less than adjacent ends of both the conical screw and the first end of the cannula. The second end of the cannula extends from the second end of the elongated tubular portion and is provided with a stop that stops axial motion of the tubular portion in a direction toward the second end of the cannula past the stop. The stop may comprise a nut that engages the cannula and against which the first end of the elongated tubular portion abuts. The nut may have an outer diameter smaller than an inner diameter of the central bore in the plug whereby the plug can travel over the nut.

When the medical instrument is a gynaecological instrument, the cannula is an intra-uterine cannula and the conical screw, screws into the cervix.

BRIEF DESCRIPTION OF THE DRAWINGS

An embodiment of the present invention will now be described, by way of example only, with reference to the accompanying drawings in which:

FIG. 2 is a plan view of a cervical funnel incorporated in the medical instrument shown in FIG. 1;

FIG. 3 is a section view of the cervical funnel shown in FIG. 2;

FIG. 4 is a perspective view of the cervical funnel shown in FIGS. 2 and 3;

FIG. 5 is a plan view of an intra-uterine cannula incorporated in the medical instrument shown in FIG. 1;

FIG. 6 is a longitudinal section view of the cannula shown in FIG. 5; and,

FIG. 7 is a side view of a plug incorporated in the instrument shown in FIG. 1.

DETAILED DESCRIPTION OF THE PREFERRED EMBODIMENTS OF THE INVENTION

Figure 1:
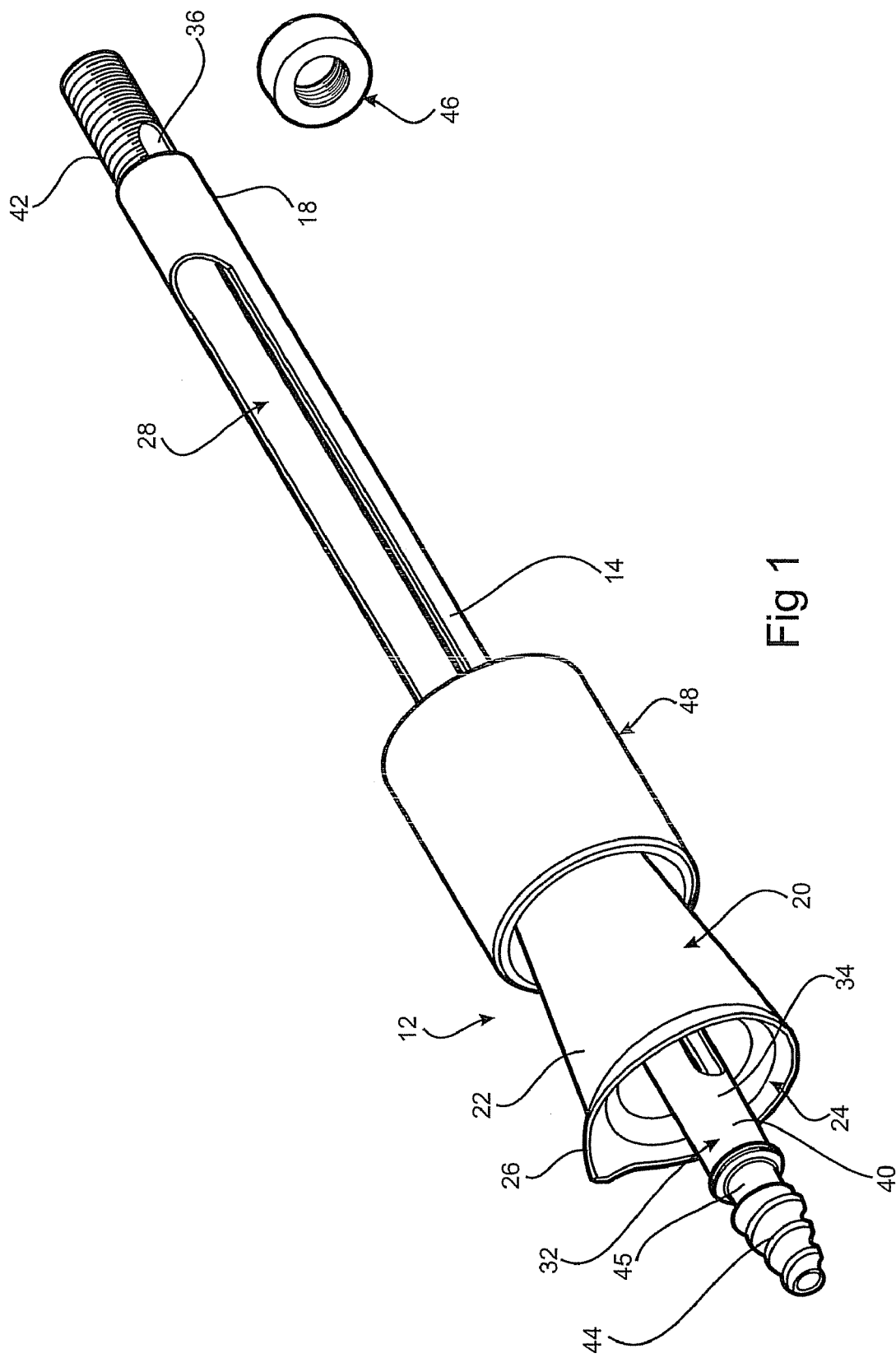
FIG. 1 is a perspective view of an embodiment of the medical instrument for gynaecological surgery.

In the following description the embodiments are described with reference to application in a gynaecological procedure, and in particular to laparoscopic hysterectomy. However embodiments are not limited in use to such a procedure and may be used in general surgery or indeed in non surgical procedures such as gynaecological examinations.

With reference to the accompanying drawings, and in particular FIGS. 1 to 4, the medical instrument 10 in accordance with an embodiment of the invention comprises a funnel 12 having an elongated tubular portion (hereinafter simply referred to as "tube") 14 with opposite first and second ends 16 and 18, respectively, and a conical portion 20 at the first end 16. The conical portion 20 has a conical outer surface 22 which increases in outer diameter in a direction from the second end 18 to the first end 16. This direction also corresponds with the direction of insertion of the instrument 10 into the vagina when the instrument 10 is used in gynaecological procedures. The conical portion 20 has a mouth 24 at an end distant the end 16 and a lip 26 that extends about a part of the circumference, or arc length, of the mouth 24. The lip 26 protrudes, or extends radially, from the conical outer surface 22. A first grip 28 is formed on the tube 14. The grip 28 not only provides a surgeon with a mechanism to easily grip the tube 14 to allow its axial sliding and rotation, it also provides a visual reference to the lip 26.

The visual reference provided by the grip 28 arises by forming the grip 28 in alignment with the lip 26, and more particularly in alignment with a mid-point of the lip 26. In this particular embodiment the grip 28 is in the form of a single elongated slot or cut-out 30 that extends axially for a portion of the length of the tube 14. It can be seen that the cut-out 30 lies inboard of the ends 18 and 16 of the tube 14 and penetrates through the thickness of the wall of the tube 14.

However, it is envisaged that in alternative embodiments the grip 28 may be formed as two or more axially aligned cut-outs or one or more axially aligned grooves that do not penetrate through the full thickness of the wall of the tube 14. In yet further variations, the grip 28 can comprise a plurality of grooves or cut-outs or both that are spaced circumferentially about the tube 14, but where one or a plurality of grooves or cut-outs are located in alignment with the lip 26 and are visually distinct from the circumferentially spaced grooves or cut-outs. This can be achieved, for example, by forming the grooves or cut-outs that are in alignment with the lip 26 to be longer or wider or both than the circumferentially spaced grooves or cut-outs.

The funnel 12 is formed as a unitary or single-piece device. This can be achieved, for example, by forming the funnel 12 from a plastics material using a moulding process. In one embodiment of the funnel 12, the lip 26 may extend about 8 mm in the axial direction from the mouth 24 and protrude or kick up from the conical surface 22 by an angle θ in the order of 156°. A typical length of the funnel 12 is 255 mm with the tube 14 having an outer diameter of approximately 16 mm and an inner diameter of 13 mm. The cut-out 30 which forms the grip 28 may run for a length of about 130 mm.

FIGS. 1, 5 and 6 also illustrate a cannula 32 incorporated in the instrument 10. The cannula 32 comprises an outer sheath 34 that is dimensioned to slide axially through, and be rotatable within, the tube 14. The cannula 32 is provided with a second grip 36 extending axially along a length of the sheath 34. The grip 36 can take any one of the forms of the grip 28 described hereinabove. However, in this particular illustrated embodiment, the second grip 36 comprises an elongate slot or cut-out 38 that terminates inboard of opposite ends 40 and 42 of the sheath 34.

A conical screw 44 is provided near the end 40 of the cannula 32. When in use for gynaecological procedures, the conical screw 44 screws into the cervix to form a seal and to thus provide fixation to the cervical canal. A reduced diameter portion or neck 45 is formed between the conical screw 44 and the end 40. The neck 45 allows the cervix to clamp back down onto the cannula 32 resulting in a secondary hold on the cervix. The cannula 32 is of a length so that when it is disposed within the funnel 12, the conical screw 44 can extend beyond the mouth 24, while the end 42 of the cannula 32 extends beyond the end 18 of the tube 14, as shown in FIG. 1.

The cannula 32, or more particularly the instrument 10, is provided with a stop in the form of a nut 46 and engages the end 42 of the cannula 32. This engagement is by way of mating screw threads formed on an outer surface of the cannula 32 adjacent the end 42. The nut 46 screws onto the end 42 and forms an abutment surface for the funnel 12. It will be appreciated that the funnel 12 cannot slide axially toward end 42 past the nut 46. Thus, by adjusting the position of the nut 46, a surgeon can set the maximum distance between the lip 26 and the conical screw 44. For reasons that will be explained in greater detail below, the nut 46 is formed with an outer diameter approximately the same as that of the tube 14.

FIGS. 1 and 7 depict a plug 48 incorporated in the instrument 10. When the instrument 10 is used in gynaecological procedures the plug 48 acts as a vaginal plug and forms a seal about its outer surface with a vaginal wall, and another seal between its inner surface and the surface 22. More particularly, the plug 48 has an inner surface of a complementary shape and configuration to that of the conical surface 22. Thus, when the plug 48 is pushed against the surface 22, a seal is formed between the surfaces 22 and 50. In order for the plug 48 to be pushed onto the surface 22, the plug is provided with an axial bore 52. The outer diameter of the nut 46 is arranged to be less than the inner diameter of the bore 52 so that the plug 48 can be removed and applied without the need to remove the nut 46. The plug 48 is provided with a cylindrical outer surface 54 that, as explained above, forms a seal against the vaginal wall.

When the instrument 10 is being used in say laparoscopic hysterectomy, initially the cannula 32 together with a manipulation shaft (not shown) is inserted into the vagina and the cannula 32 rotated so that the conical screw 44 engages the cervix to seal the uterus. The manipulation shaft is in the form of an elongated rod that extends or passes through a central bore formed in the cannula 32 and is provided at one end with a curved smooth surface. This prevents the manipulation shaft from slipping back through the cannula 32 and facilitates distension of the uterus. An opposite end of the manipulation shaft extends from end 42 of the cannula 32 to allow it to be gripped and rotated and/or slid axially.

The funnel 12 is then inserted into the vagina over the cannula 32. During a surgical procedure the lip 26 can be positioned to lift a section of the vaginal wall away from internal organs such as the bladder and bowel. Rotation of the funnel 12 allows appreciation of where the vaginal wall is in relation to the bladder. In addition, rotation of the lip 26 stretches the vaginal wall. The lip 26 forms a cutting edge in the sense that tissue is cut, using another cutting instrument, against the lip 26; that is, the lip 26 forms a backing, support or boundary for tissue while it is being cut. The grip 36 allows easy rotation of the cannula 32 while the conical screw 44 is being screwed into and out of the cervix. It is particularly beneficial when unscrewing as the cannula 32 is likely to be covered with blood or other liquids, making gripping difficult. Further, the grip 28 in the funnel 12 facilitates easier insertion and subsequent rotation of the funnel 12 during the surgical procedure, which again may otherwise be difficult due to the presence of blood or other liquids. The grip also provides a surgeon with a visual reference to the location of the lip 26 which may otherwise be problematic during various procedures including a laparoscopic procedure.

The stop 46 is screwed onto the end 42 to form an abutment surface for the funnel 12 and thereby set the distance between the conical screw 44 and the lip 46. This of course can be adjusted during surgery, if necessary, by simple rotation of the nut 46. The plug 48 can be slid over the tube 14 and inserted into the vagina to form a seal between the vaginal wall and the conical portion 20 of the instrument 10.

Both the funnel and the cannula 32 may be made from plastics material using a moulding process. This facilitates the production of a single-use instrument 10.

All modifications and variations to the above-described embodiment that would be obvious to a person of ordinary skill in the art are deemed to be within the scope of the present invention, the nature of which is to be determined from the above description.

The invention claimed is:

1. A medical instrument comprising:
    a funnel having an elongated tubular portion and an integrally formed conical portion at one end thereof, the conical portion having a conical outer surface which progressively increases in outer diameter from the one end to a lip located at a distal end of the conical portion, wherein the lip extends about a part of a circumference of the conical outer surface at the distal end and protrudes from the conical outer surface; and
    a first grip formed on the elongated tubular portion, the first grip being an axially extending cut-out formed in the elongated tubular portion and in alignment with a midpoint of an outer most edge of the lip, the funnel being hollow for an entirety of its length forming a passage arranged to receive a cannula, and wherein the cut-out provides access to the passage.

2. The medical instrument according to claim 1, wherein the cut-out is one of two or more axially aligned cut-outs.

3. The medical instrument according to claim 1, further comprising a plug having an inner surface of complementary shape and configuration to the conical outer surface; and, a central bore, whereby the elongated tubular portion passes through the central bore, and the inner surface when pushed onto the outer surface, forms a seal therewith.

4. The medical instrument according to claim 3, wherein the plug comprises an outer cylindrical surface which forms a seal with surrounding tissue of a body cavity or opening to thereby plug the cavity or opening.

5. The medical instrument according to claim 1, wherein the funnel is made from a plastics material.

6. The medical instrument according to claim 1, further comprising a cannula having an outer sheath dimensioned to slide axially through, and be rotatable within, the elongated tubular portion, the cannula provided with a second grip extending axially along a length of the outer sheath.

7. The medical instrument according to claim 6, wherein the second grip comprises a portion in the form of one or more axially extending grooves, or one or more axially extending cut-outs, in the outer sheath.

8. The medical instrument according to claim 7, wherein when the portion of the second grip comprises more than one groove or more than one cut-out, two or more of the grooves or the cut-outs are positionable to be axially aligned.

9. The medical instrument according to claim 6, wherein the second grip comprises a single elongated cut-out having opposite ends that terminate inside of respective opposite ends of the outer sheath.

10. The medical instrument according to claim 6, wherein the cannula comprises:
    first and second ends;
    a conical screw near the first end of the cannula for screwing into an opening of, or formed in an organ or other tissue, the conical screw reducing in diameter in a direction from the second end to the first end; and
    a neck located between the conical screw and the first end of the cannula, the neck having a diameter less than adjacent ends of both the conical screw and the first end of the cannula.

11. The medical instrument according to claim 10, wherein the second end of the cannula extends from the second end of the elongated tubular portion and is provided with a stop that stops axial motion of the tubular portion in a direction toward the second end of the cannula past the stop.

12. The medical instrument according to claim 11, wherein the stop comprises a nut that engages the cannula and which the first end of the elongated tubular portion abuts.

13. The medical instrument according to claim 12, wherein the nut has an outer diameter about the same as an outer diameter of the tubular portion.

* * * * *